United States Patent [19]
Aisaka et al.

[11] Patent Number: 5,776,739
[45] Date of Patent: Jul. 7, 1998

[54] PROCESS FOR PRODUCING DISACCHARIDES AND NOVEL DISACCHARIDES

[75] Inventors: Kazuo Aisaka; Yutaka Saitoh; Youichi Uosaki, all of Tokyo, Japan

[73] Assignee: Kyowa Hakko Kogyo Co., Ltd., Tokyo, Japan

[21] Appl. No.: 596,262

[22] PCT Filed: Dec. 8, 1994

[86] PCT No.: PCT/JP94/02060

§ 371 Date: Jul. 5, 1996

§ 102(e) Date: Jul. 5, 1996

[87] PCT Pub. No.: WO95/34570

PCT Pub. Date: Dec. 21, 1995

[30] Foreign Application Priority Data

Jun. 10, 1919 [JP] Japan ................................. 6-128483

[51] Int. Cl.⁶ .............................. C12P 19/12; C07H 3/04
[52] U.S. Cl. ..................................... 435/100; 536/123.13
[58] Field of Search ........................ 435/100; 536/123.13

[56] References Cited

U.S. PATENT DOCUMENTS 5,565,341  10/1996  Takahashi et al. ..................... 435/100

FOREIGN PATENT DOCUMENTS 50-154485  12/1975  Japan .
58-216695  12/1983  Japan .
88060998  11/1988  Japan .

OTHER PUBLICATIONS

Chemical Abstract of Japanese patent 08280395 A2 (Ajinimoto), Oct. 1996.

Colaco et al. "Extraordinary stability of enzymes dried in trehalose: Simplified Molecular Biology," Bio/Technology 10: 1007–1011, 1992.

Selinger, et al. "Enzymatic synthesis of the maltose analogues, glucosyl ...", J. Biol. Chem. 236: 2183–2185, 1961.

*Primary Examiner*—Mary E. Ceperley
*Attorney, Agent, or Firm*—White & Case

[57] ABSTRACT

A process for producing a disaccharide which comprises: conducting the condensation reaction of β-glucose-1-phosphate with a monosaccharide in an aqueous medium in the presence of an enzyme source which is derived from a microorganism belonging to the genus Catellatospora, Kineosporia, Propionibacterium, or Enterococcus and which has sugar phosphorylase activity; and recovering the disaccharide formed in the aqueous medium, as well as a novel disaccharide obtained by the process. The disaccharide obtained by the present invention is useful as a stabilizer for medicine, food, cosmetic and enzyme.

8 Claims, No Drawings

PROCESS FOR PRODUCING DISACCHARIDES AND NOVEL DISACCHARIDES

TECHNICAL FIELD

The present invention relates to a process for producing disaccharides. The disaccharides are useful as a component of medicines, foods, and cosmetics, etc., and as an enzyme stabilizer in diagnostic reagents, etc.

BACKGROUND OF THE INVENTION

As a process for producing disaccharides having α,1-1 glucoside bond, there has been known a process for producing trehalose [glucosyl(α,1-1)D-glucose] using a microorganism belonging to the genus Nocardia (Japanese Published Unexamined Patent Application No. 154485/75) and a process for producing trehalose by treating maltose [glucosyl(α,1-4)D-glucose] with maltose phosphorylase (hereinafter, referred to as MP) and trehalose phosphorylase (hereinafter, referred to as TP) (Japanese Published Examined Patent Application No. 60998/88). As a process for producing disaccharides having α,1-4 glycoside bond, there has been known a process for producing maltose derivatives using an extract derived from *Neisseria perflava* [J. Biol. Chem., 236, 2183–2185 (1961)].

However, in the process using the microorganism belonging to the genus Nocardia, only a slight amount of trehalose is produced in the culture medium, and in the process for producing disaccharides by the treatment of maltose with MP and TP, disaccharides other than trehalose cannnot be produced. In the process using an extract derived from *Neisseria perflava*, the substrate β-glucose-1-phosphate is obtained by the phosphorolysis of maltose, however, the process requires a step of removing glucose formed as a by-product.

The disaccharides such as trehalose and maltose are known to enhance the stability of biopolymers such as enzyme proteins [C.Colaco et al., Bio/Technology, 10, 1007–1011, (1992)].

DISCLOSURE OF THE INVENTION

The present invention provides a process for producing disaccharides which comprises: conducting the condensation reaction of β-glucose-1-phosphate with a monosaccharide in an aqueous medium in the presence of an enzyme source which is derived from a microorganism belonging to the genus Catellatospora, Kineosporia, Propionibacterium, or Enterococcus and which has sugar phosphorylase activity; and recovering the disaccharide formed in the aqueous medium. The present invention further provides disaccharides obtained by the process of the present invention.

The present invention is described in detail below.

The enzyme source employed in the present invention includes a culture, cells or processed cells of a microorganism having sugar phosphorylase activity or an enzyme having sugar phosphorylase activity.

As the microorganism having the sugar phosphorylase activity, any microorganism may be employed, so long as it belongs to the genus Catellatospora, Kineosporia, Propionibacterium, or Enterococcus and it is capable of producing an enzyme having the sugar phosphorylase activity. Examples of such microorganism include TP-producing microorganisms such as *Catellatospora ferruginea* KY2039 and *Kineosporia aurantiaca* ATCC 29727 and MP-producing microorganisms such as *Propionibacterium freudenreichii* KY4002 and *Enterococcus faecium* ATCC 10541.

The bacteriological properties of the species of the microorganisms listed above are described in Int. J. Syst. Bacteriol., 36, 512–517 (1986) for *Catellatospora ferruginea*, Bergey's Manual of Systematic Bacteriology, Vol.4, 2504–2506 (1989) for *Kineosporia aurantiaca*, Bergey's Manual of Systematic Bacteriology, Vol.2, 1346–1350 (1986) for *Propionibacterium freudenreichii* and Bergey's Manual of Systematic Bacteriology, Vol.2, 1063–1065 (1986) for *Enterococcus faecium*.

*Catellatospora ferruginea* KY2039 and *Propionibacterium freudenreichii* KY4002 were deposited with National Institute of Bioscience and Human-Technology, Agency of Industrial Science and Technology, Japan on Jun. 11, 1993, under the Budapest Treaty, with the accession numbers FERM BP-4329 and FERM BP-4330, respectively.

As the medium employed to obtain the enzyme source having sugar phosphorylase activity, any of natural or synthetic medium may be employed, so long as it contains suitable amounts of carbon sources, nitrogen sources, minerals and other nutritients.

As the carbon source, carbohydrates such as glucose, sucrose, trehalose, maltose, starch and molasses, alcohols such as glycerol, sorbitol and mannitol, and organic acids such as acetic acid, lactic acid, pyruvic acid and citric acid may be employed.

As the nitrogen source, inorganic and organic ammonium salts such as ammonia, ammonium chloride, ammonium carbonate, ammonium phosphate and ammonium acetate, nitrogen compounds such as urea and amino acids, and nitrogen-containing organic materials such as peptone, NZ-amine, meat extract, corn steep liquor and casein hydrolysate may be employed.

As the mineral, potassium dihydrogen phosphate, potassium hydrogen phosphate, potassium chloride, sodium chloride, magnesium phosphate and ferrous sulfate may be employed.

Culturing may be conducted by standing culture or spinner culture with aeration. The temperature is kept in the range of 25° to 37° C. and the pH of the culture medium is kept in the range of 6.0 to 8.0. The culturing is completed usually in 1 to 7 days.

After completion of the culturing, for the production of the disaccharides, a culture, cells or processed cells of the obtained microorganism may be used as it is or it may be converted to crude or purified enzyme.

Examples of the processed cells of the microorganism are dried cells, freeze-dried cells, surfactant-treated cells, enzymatically-treated cells, ultrasonically treated cells, mechanically ground cells, mechanically pressured cells, protein containing fractions of the cells, and immobilized products of cells or processed cells.

Any of crude or purified enzyme may be used as the enzyme, and the enzyme is obtained by subjecting the processed cells of the microorganism to a process usually employed for purifying the enzymes, such as salting out, organic solvent sedimentation, dialysis, ion exchange, column chromatography, gel filtration and freeze-drying.

As the enzyme having the sugar phosphorylase activity, any enzyme may be employed, so long as it catalyzes the condensation reaction of β-glucose-1-phosphate with a monosaccharide to yield a disaccharide such as TP and MP.

The enzyme source having the sugar phosphorylase activity is employed in an aqueous medium as wet cells in the range of 1 to 100 g/L, preferably 10 to 50 g/L, or as enzyme activity in the range of 0.1 to 100 units/ml, preferably 1 to 10 units/ml.

The enzyme activity of the enzyme having the sugar phosphorylase activity is represented in units, with a unit being defined as the activity capable of producing 1 μmol of glucose when TP and MP, for example, are reacted in 50 mM phosphate buffer (pH 6.5) at 37° C. for 1 minute in the presence of trehalose and maltose, respectively, as the substrates.

The aqueous medium includes water, buffers such as phosphate, carbonate, acetate, borate, citrate and tris, alcohols such as methanol and ethanol, esters such as ethyl acetate, ketones such as acetone, amides such as acetoamide, and natural or synthetic medium containing carbon sources, nitrogen sources and inorganic salts which can be assimilated by the microorganisms. If necessary, a surfactant such as cetylpyridium chloride and cetyltrimethylammonium bromide may be added to the concentration of 0.05 to 1.0% (w/v) and an organic solvent such as toluene and xylene may be added to the concentration of 1 to 20% (v/v).

As the monosaccharide, any of crude or purified materials may be employed. For example, D-glucose, D-fucose, D-xylose, D-mannose, D-allose, D-tagatose, D-sorbose, D-glucosamine, 2-deoxy-D-glucose, N-acetyl-D-glucosamine or L-fucose is employed in the range of 1 to 100 g/L, preferably in the range of 10 to 50 g/l.

β-glucose-1-phosphate is employed in the range of 1 to 100 g/L, preferably 10 to 50 g/L. Although commercially available β-glucose-1-phosphate may be employed, β-glucose-1-phosphate, which is obtained by converting maltose into glucose and β-glucose-1-phosphate in an aqueous medium in the presence of an enzyme source having MP activity and an enzyme source having glucose decomposition activity and then by decomposing the glucose produced in the aqueous medium in the presence of an enzyme source having the glucose decomposition activity, may also be employed.

The enzyme source having MP activity may be contained in the aqueous medium as wet cells in the range of 10 to 100 g/L, preferably 20 to 50 g/L, or as enzyme activity in the range of 1 to 100 units/ml, preferably 10 to 50 units/ml, per 1 mol of maltose.

The amount of the enzyme source having the glucose decomposition activity contained in the aqueous medium is such that the glucose produced by conversion of maltose with the enzyme source having MP activity can be decomposed completely.

The enzyme source having the glucose decomposition activity includes a microorganism having glucose decomposition activity, a culture, cells or processed cells of such microorganism and an enzyme having glucose decomposition activity.

As the microorganism having glucose decomposition activity, any microorganism may be employed, so long as it is capable of producing an enzyme having glucose decomposition activity, among those, yeast is preferably employed.

The enzyme having glucose decomposition activity, includes glucose oxidase, catalase, pyranose oxidase, glucose dehydrogenase, glucokinase and hexokinase. Among those, glucose oxidase or catalase is preferably employed.

In the production of β-glucose-1-phosphate, maltose is reacted in an aqueous medium in the presence of an enzyme source having maltose phosphorylase activity and an enzyme source having glucose decomposition activity usually at 20° to 60° C., preferably 30° to 50° C., and at a pH of 5.0 to 9.0, preferably 6.0 to 7.5 for 1 to 72 hours.

After completion of the reaction, β-glucose-1-phosphate formed in the aqueous medium is subjected to condensation with a monosaccharide in the presence of an enzyme source having the sugar phosphorylase activity. β-glucose-1-phosphate may be used for reaction, after it is isolated by removing precipitates such as cells from the aqueous medium by means of centrifugation and subjecting the obtained supernatant to a usual method such as ion-exchange column chromatography and concentration. Alternatively, β-glucose-1-phosphate may be reacted directly as dissolved in the aqueous medium.

In the production of the disaccharide, the reaction of β-glucose-1-phosphate with a monosaccharide in an aqueous medium in the presence of an enzyme source having sugar phosphorylase activity is usually conducted at 20° to 60° C., preferably 30° to 50° C., and at a pH of 5.0 to 9.0, preferably 6.0 to 7.5 for 1 to 72 hours.

After the completion of the reaction, the disaccharide can be obtained by removing precipitates such as cells from the aqueous medium by means of centrifugation, and subjecting the supernatant to a usual method such as ion-exchange column chromatography and concentration.

Depending on the monosaccharide employed in the reaction, the present invention provides known disaccharides such as trehalose and maltose and novel disaccharides such as glucosyl (α, 1-1)D-fucose, glucosyl (α, 1-4)D-mannose, glucosyl (α, 1-4)D-allose, glucosyl (α, 1-4)D-tagatose, glucosyl (α, 1-4)L-fucose and glucosyl (α, 1-4)D-sorbose.

Among the disaccharides listed above, trehalose, maltose, glucosyl (α, 1-1)D-fucose and glucosyl (α, 1-4)L-fucose were evaluated for their effects on the stability of an enzyme such as alkaline phosphatase under the follwoing condition:

(1) stored as a solution, (2) stored in frozen form, (3) frozen and thawed repeatedly and (4) stored as dried powder, in the following Test Examples.

TEST EXAMPLE 1

A sample solution (unsupplemented) was prepared by diluting alkaline phosphatase (derived from calf small intestine, Boehringer Mannheim Biochemica) with distilled water. Other sample solutions were prepared by adding, to the above solution, trehalose, maltose, glucosyl (α, 1-1)D-fucose or glucosyl (α, 1-4)L-fucose to the concentration of 50 mM. The sample solutions were allowed to stand at room temperature (25° C.) for 24 hours, and the activity of alkaline phosphatase in each of the sample solutions was determined.

The activity of alkaline phosphatase was determined as follows.

Each of the sample solutions (10 μl) was incubated at 37° C. in 2.0 ml of the reaction mixture consisting of 1M diethanol-amine buffer (pH 10.2), 0.2 mM magnesium chloride and 5 mM p-nitrophenyl phosphoric acid. Then, the enzyme activity was determined by the amount of p-nitrophenol produced therein, which was culculated on the basis of change in absorbance at 405 nm. The activity of each of the sample solutions immediately after the preparation was defined as 100%, and the residual activity in the stored sample solution was calculated.

The results are shown in Table 1.

TABLE 1

| Sugar (50 MM) | Residual activity (%) |
|---|---|
| Unsupplemented | 0 |
| Trehalose | 9.4 |
| Maltose | 3.3 |
| Glucosyl (α, 1-1) D-fucose | 21.8 |
| Glucosyl (α, 1-4) L-fucose | 93.7 |

TEST EXAMPLE 2

A sample solution (unsupplemented) was prepared by diluting alkaline phosphatase with distilled water. Other sample solutions were prepared by adding, to the above solution, trehalose, maltose, glucosyl (α, 1-1)D-fucose or glucosyl (α, 1-4)L-fucose to the concentration of 50 mM. The sample solutions were stored in frozen form at −20° C. for 6 days. After thawing at room temperature, the activity of alkaline phosphatase in each of the sample solutions was determined in a manner similar to that employed in Test Example 1. The activity of each of the sample solutions immediately after preparation was defined as 100%, and the residual activity in the stored sample solution was calculated.

The results are shown in Table 2.

TABLE 2

| Sugar (50 MM) | Residual activity (%) |
|---|---|
| Unsupplemented | 2.0 |
| Trehalose | 26.4 |
| Maltose | 20.0 |
| Glucosyl (α, 1-1) D-fucose | 36.3 |
| Glucosyl (α, 1-4) L-fucose | 76.0 |

TEST EXAMPLE 3

A sample solution (unsupplemented) was prepared by diluting alkaline phosphatase with distilled water. Other sample solutions were prepared by adding, to the above solution, trehalose, maltose, glucosyl (α, 1-1)D-fucose or glucosyl (α, 1-4)L-fucose to the concentration of 50 mM. Each of the sample solutions was frozen by dry ice/ethanol and thawed at room temperature repeatedly 10 times in total. The activity of alkaline phosphatase in each of the sample solutions was determined in a manner similar to that employed in Test Example 1. The activity of each of the sample solutions immediately after the preparation was defined as 100%, and the residual activity in the frozen and thawed sample solution was calculated.

The results are shown in Table 3.

TABLE 3

| Sugar (50 MM) | Residual activity (%) |
|---|---|
| Unsupplemented | 10.3 |
| Trehalose | 21.6 |
| Maltose | 16.3 |
| Glucosyl (α, 1-1) D-fucose | 65.0 |
| Glucosyl (α, 1-4) L-fucose | 106.0 |

TEST EXAMPLE 4

A sample solution (unsupplemented) was prepared by diluting alkaline phosphatase with distilled water. Other sample solutions were prepared by adding, to the above solution, trehalose, maltose, glucosyl (α, 1-1)D-fucose or glucosyl (α, 1-4)L-fucose to the concentration of 50 mM. Each of the sample solutions was evaporated at room temperature to dryness using a vacuum pump to obtain dry powder, and the dry powder was stored at 50° C. for 24 hours. The activity of alkaline phosphatase in each of the sample solutions was determined in a manner similar to that employed in Test Example 1. The activity of each of the sample solutions immediately after preparation was defined as 100%, and the residual activity in the stored sample solution was calculated.

The results are shown in Table 4.

TABLE 4

| Sugar (50 MM) | Residual activity (%) |
|---|---|
| Unsupplemented | 12.6 |
| Trehalose | 55.0 |
| Maltose | 41.0 |
| Glucosyl (α, 1-1) D-fucose | 62.5 |
| Glucosyl (α, 1-4) L-fucose | 83.0 |

As is evident from the results shown above, trehalose, maltose, glucosyl (α, 1-1)D-fucose and glucosyl (α, 1-4)L-fucose, especially glucosyl (α, 1-1)D-fucose and glucosyl (α, 1-4)L-fucose, are effective as a stabilizer for alkaline phosphatase.

BEST MODE FOR CARRYING OUT THE INVENTION

Example 1

A reaction mixture consisting of 50 mM imidazole-HCl buffer (pH 7.0), 50 mM β-glucose-1-phosphate, 50 mM monosaccharide (D-glucose, D-fucose or D-xylose) and 2 units/ml purified TP enzyme derived from Catellatospora ferruginea or a reaction mixture consisting of 50 mM imidazole-HCl buffer (pH 7.0), 50 mM β-glucose-1-phosphate, 50 mM monosaccharide (D-glucose, 2-deoxy-D-glucose, D-glucosamine, N-acetyl-D-glucosamine, D-mannose, D-allose, D-tagatose, D-sorbose, L-fucose or D-xylose) and 2 units/ml purified MP enzyme derived from Propionibacterium freudenreichii was reacted at 30° C. for 4 hours.

After the completion of the reaction, the reaction mixture was centrifuged to obtain the supernatant, which was then subjected to HPLC to isolate the disaccharide. The isolated disaccharide was then identified and quantified directly using the respective standards in case of a known substance. In case of a novel substance, the isolated disaccharide was subjected to either acid hydrolysis by boiling in 1N sulfuric acid at 100° C. for 1 hour or enzymatic decomposition using α-glucosidase to obtain the monosaccharide as the constituent of the disaccharide, which was identified and quantified using HPLC. HPLC was conducted under the condition shown below.

Column: Shim-pack CLC-NH₂ (6 mm×15 cm) (Shimadzu Corporation) Mobile phase: 80% Acetonitrile—20% water Flow rate: 1 ml/min. Detector: Differential refractometer (Shimadzu Corporation)

The monosaccharides added to the reaction mixtures, reaction products and yields are shown in Table 5.

TABLE 5

| Monosaccharide | Enzyme | Disaccharide (Reaction product) | Yield(%) |
|---|---|---|---|
| D-Glucose | TP | Glucosyl (α, 1-1) D-glucose(Trehalose) | 70.0 |
| D-Fucose | TP | Glucosyl (α, 1-1) D-fucose | 18.9 |
| D-Xylose | TP | Glucosyl (α, 1-1) D-xylose | 35.1 |
| D-Glucose | MP | Glucosyl (α, 1-4) D-glucose(Maltose) | 80.0 |
| 2-Deoxy-D-glucose | MP | Glucosyl (α, 1-4) 2-deoxy-D-glucose | 62.6 |
| D-Glucosamine | MP | Glucosyl (α, 1-4) D-glucosamine | 39.8 |
| N-Acetyl-D-glucosamine | MP | Glucosyl (α, 1-4) N-acetyl-D-glucosamine | 54.2 |
| D-Mannose | MP | Glucosyl (α, 1-4) D-mannose | 50.5 |
| D-Allose | MP | Glucosyl (α, 1-4) D-allose | 13.0 |
| D-Tagatose | MP | Glucosyl (α, 1-4) D-tagatose | 10.9 |
| D-Sorbose | MP | Glucosyl (α, 1-4) D-sorbose | 37.3 |
| L-Fucose | MP | Glucosyl (α, 1-4) L-fucose | 36.0 |
| D-Xylose | MP | Glucosyl (α, 1-4) D-xylose | 85.6 |

Example 2

A reaction mixture consisting of 50 mM phosphate buffer (pH 6.5), 50 mM maltose, 100 mg wet cells/ml *Catellatospora ferruginea* KY2039, 10 mg of wet cells/ml *Propionibacterium freudenreichii* KY4002 and 0.1% cetylpyridium chloride was reacted at 30° C. for 18 hours.

After the completion of the reaction, the reaction mixture was centrifuged to obtain the supernatant, which was then analyzed using HPLC, and it was indicated that trehalose was produced at the yield of 52%.

Example 3

A reaction mixture consisting of 50 mM phosphate buffer (pH 6.5), 50 mM maltose, 1 unit/ml purified MP enzyme derived from *Propionibacterium freudenreichii* KY4002 and 2 units/ml purified TP enzyme derived from *Catellatospora ferruginea* KY2039 was reacted at 30° C. for 18 hours.

After the completion of the reaction, the reaction mixture was centrifuged to obtain the supernatant, which was then analyzed using HPLC, and it was indicated that trehalose was produced at the yield of 78%.

Example 4

A reaction mixture consisting of 50 mM of phosphate buffer (pH 6.5), 50 mM maltose, 1 unit/ml purified MP enzyme derived from *Enterococcus faecium* ATCC 10541 and 2 units/ml purified TP enzyme derived from *Kineosporia aurantiaca* ATCC 29727 was reacted at 30° C. for 18 hours.

After the completion of the reaction, the reaction mixture was centrifuged to obtain the supernatant, which was then analyzed using HPLC, and it was indicated that trehalose was produced at the yield of 75%.

Example 5

A reaction mixture consisting of 50 mM phosphate buffer (pH 6.5), 50 mM maltose, 1 unit/ml purified MP enzyme derived from *Propionibacterium freudenreichii* KY4002, 2 units/ml glucose oxidase (Toyobo Co., Ltd.) and 3000 units/ml catalase (Sigma Chemical Company) was reacted at 30° C. for 6 hours, whereby producing β-glucose-1-phosphate and glucose from maltose while decomposing the produced glucose with glucose oxidase and catalase. To the reaction mixture was added purified TP enzyme derived from *Catellatospora ferruginea* KY2039 and D-fucose to the concentration of 2 units/ml and 200 mM, respectively, and reacted for further 18 hours.

After the completion of the reaction, the reaction mixture was centrifuged to obtain the supernatant, which was then analyzed using HPLC, and it was indicated that glucosyl (α, 1-1)D-fucose was produced at the concentration of 29 mM.

Example 6

A reaction mixture consisting of 50 mM phosphate buffer (pH 6.5), 50 mM maltose, 2 units/ml purified MP enzyme derived from *Propionibacterium freudenreichii* KY4002, 2 units/ml glucose oxidase and 3000 units/ml catalase was reacted at 30° C. for 6 hours, whereby producing β-glucose-1-phosphate and glucose from maltose while decomposing the produced glucose with glucose oxidase and catalase. To the reaction mixture was added L-fucose to the concentration of 200 mM, and reacted for further 18 hours.

After the completion of the reaction, the reaction mixture was centrifuged to obtain the supernatant, which was then analyzed using HPLC, and it was indicated that glucosyl (α, 1-4)L-fucose was produced at the concentration of 38 mM.

Example 7

Activated carbon (500 g, Nacalai Tesque, Inc.) and a filtration aid, HI-FLO Supercell (500 g, Nacalai Tesque, Inc.), were dispersed thoroughly in distilled water and the microparticles were decanted off. Then, the dispersion was packed into a column of 50 cm in length and an inner diameter of 5 cm, which was then washed with about 3 L of 3% butanol, and further washed with 3 L of water. Then, 200 ml of the solution of glucosyl (α, 1-1)D-fucose obtained in Example 5 was loaded into the column, which was then washed with about 2 L of distilled water and about 2 L of 0.2% propanol solution, and subsequently eluted with 5% propanol to obtain the target substance. After freeze-drying the eluent, about 1 g of glucosyl (α, 1-1)D-fucose was obtained as white powder.

The physical properties of glucosyl(α,1-1)D-fucose are shown below.

Appearance: Colorless powder

Specific rotation: $[\alpha]D^{20}$=+189° (c=0.309, $H_2O$), No time course change (No mutarotation)

FABMS spectrum (Negative mode, Matrix: glycerol): m/z amu 325(M-H)–

High resolution FABMS spectrum (Negative mode, Matrix: glycerol): m/z amu Found: 325.1121 (M-H)–Calculated as $C_{12}H_{21}O_{10}$: 325.1135

IR spectrum(KBr): $\upsilon_{max}cm^{-1}$: 3410, 2935, 1653, 1419, 1385, 1080, 1005, 966

$^{13}C$ NMR spectrum(125 MHz,$D_2O$): δppm from TMS 94.40, 94.24, 73.41, 72.95, 72.67, 71.94, 70.54, 69.99, 68.54, 67.94, 61.37, 16.09

¹H NMR spectrum (500 MHz,D₂O): δppm from TMS 5.19 (2H, d, J=3.9 Hz), 4.23 (1H, q, J=6.5Hz), 4.05 (1H, dd, J=10.4, 3.4 Hz), 3.91 (1H, dd, J=10.4, 3.9 Hz), 3.89 (1H,m), 3.88 (2H,m), 3.86 (1H,m), 3.80 (1H, dd, J=11.6, 4.8 Hz), 3.68 (1H, dd, J=9.9,3.9 Hz), 3.48 (1H, t, J=9.4 Hz), 1.26 (3H, d, J=6.5 Hz)

Example 8

Purification process was conducted in a manner similar to that employed in Example 7 except that glucosyl (α, 1-4) L-fucose obtained in Example 6 was used instead of glucosyl (α, 1—1)D-fucose solution obtained in Example 5 to give about 2 g of glucosyl (α, 1-4)L-fucose as white powder.

The physical properties of glucosyl (α, 1-4)L-fucose are shown below.
Appearance: Colorless powder
Melting point: 117.0 to 120.5° C.
Specific rotation: $[\alpha]D^{20}=+39.2°$ (c=0.335, H₂O), Final value (after 24 hours)
FABMS spectrum (Negative mode, Matrix: glycerol): m/z amu 325 (M-H)⁻
High resolution FABMS spectrum (Negative mode, Matrix:glycerol):m/z amu Found:325.1112(M-H)-Calculated as $C_{12}H_{21}O_{10}$: 325.1135
IR spectrum (KBr): $\upsilon_{max}$cm⁻¹ 3396, 2931, 1635, 1456, 1417, 1362, 1134, 1080, 1022
¹³C NMR spectrum (100 MHz, D₂O): δppm from TMS 102.04, 102.00, 97.31, 93.45, 83.17, 82.46, 74.97, 74.15, 73.77, 73.74, 73.34, 73.30, 71.61, 71.37, 70.57, 70.54, 69.85, 67.40, 61.67, 17.45, 17.40
¹H NMR spectrum (400 MHz, D₂O): δppm from TMS 5.27 (d, J=3.9 Hz), 5.26 (d, J=4.9 Hz), 4.63 (d, J=7.8 Hz), 4.30 (q, J=6.6 Hz), 3.99(m), 3.98(m), 3.93(m), 3.93(m), 3.92(m), 3.89(m), 3.88 (q, J=6.6 Hz), 3.82(m), 3.81 (dd, J=11.8,4.5 Hz), 3.75 (dd, J=10.0,3.2 Hz), 3.65 (dd, J=9.9,3.9 Hz), 3.59 (dd, J=10.0,7.8 Hz), 3.46 (t, J=9.4 Hz), 1.33 (d, J=6.6 Hz), 1.30 (d, J=6.6 Hz)

Reference Example 1

Preparation of crude enzyme (1) *Catellatospora ferruginea* KY2039A was inoculated on 300 ml of the medium (pH 7.0) having the composition of 3 g/dl sucrose, 0.5 g/dl NZ-amine, 0.2 g/dl peptone, 0.1 g/dl yeast extract and 0.1 g/dl meat extract in a 2-L Erlenmeyer's flask and cultured with shaking at 30° C. for 48 hours. The obtained culture (600 ml) was inoculated on 15 L of the medium having the same composition as that of the above medium in a 30-L jar-fermenter and incubated with stirring and aerating at 30° C. for 3 days.

After the completion of the incubation, 15 L of the culture was centrifuged (12,000×g, 20 minutes) to obtain the cells, which were suspended in 1000 ml of 200 mM phosphate buffer (pH 7.0). The cells were ground using Dynomill (W. A. Bachofen AB), and the supernatant was obtained as crude TP enzyme by centrifugation (12,000×g, 20 minutes).

The activity of the TP crude enzyme derived from *Catellatospora ferruginea* KY2039 was 5.0 units/g of wet cells. The value was about 30 times as large as that of the crude enzyme derived from *Euglena gracilis* (0.17 units/g of wet cells, Japanese Published Examined Patent Application No. 60998/88).

(2) Crude TP enzyme was obtained using the incubation and extraction methods similar to those employed in section (1) except for using *Kineosporia aurantiaca* ATCC 29727 instead of *Catellatospora ferruginea* KY2039.

The activity of the TP crude enzyme derived from *Kineosporia aurantiaca* ATCC 29727 was 5.4 units/g of wet cells.

(3) *Propionibacterium freudenreichii* KY4002 was inoculated on 600 ml of the medium (pH 7.5) having the composition of 2 g/dl sucrose, 1 g/dl tryptone, 1 g/dl yeast extract, 0.5 g/dl dipotassium phosphate, 0.04 g/dl magnesium sulfate (heptahydrate), 0.001 g/dl manganese sulfate (tetrahydrate) and 0.005 g/dl Vitamin C in a conical flask, and allowed to stand at 30° C. for 2 days.

After the completion of the incubation, the obtained cultures were pooled to 1.2 L, and centrifuged (12,000×g, 20 minutes) to obtain the cells. The obtained cells were suspended in 300 ml of 10 mM phosphate buffer (pH 7.0). The cells were ground using Dynomill, and centrifuged (12,000× g, 20 minutes) to obtain the supernatant as crude MP enzyme.

The activity of the crude MP enzyme derived from *Propionibacterium freudenreichii* KY4002 was 55.0 units/g of wet cells. The value was about 1.8 times as large as that of the crude enzyme derived from *Lactobacillus brevis* (29.9 units/g of wet cells, Japanese Published Examined Patent Application No. 60998/88).

(4) Crude MP enzyme was obtained using the incubation and extraction methods similar to those employed in section (3) except that *Enterococcus faecium* ATCC 10541 was used instead of *Propionibacterium freudenreichii* KY4002.

The activity of the crude MP enzyme derived from *Entercocccus faecium* ATCC 10541 was 50.0 units/g of wet cells.

Reference Example 2

Preparation of Purified Enzyme (1) To crude TP enzyme derived from *Catellatospora ferruginea* KY2039 obtained in section (1) of Reference Example 1, ammonium sulfate was added to the concentration of 50% saturation to collect the precipitate. The obtained precipitate was dissolved in a small amount (about 200 ml) of 200 mM phosphate buffer (pH 7.0). The obtained solution was dialyzed against 5 L of the same buffer for 24 hours, heated at 65° C. for 15 minutes and centrifuged (12,000×g, 20 minutes) to obtain the supernatant. The obtained supernatant was loaded onto the column (1 L, diameter: 5 cm) packed with gel filter Toyopearl HW65F (Tosoh Corporation) which had previously been equilibrated with the same buffer. The eluted active fractions were combined, and ammonium sulfate was added thereto to the concentration of 50% saturation. The precipitates were collected by centrifugation (12,000×g, 20 minutes) and dissolved in 20 ml of 200 mM phosphate buffer (pH 7.0). The obtained solution was dialyzed against 2 L of the same buffer for 24 hours to obtain purified TP enzyme (specific activity: 100 mU/mg).

The specific activity of the purified TP enzyme was as 102 times as that of the crude enzyme, and the yield of the enzyme activity was 62%.

(2) Purified TP enzyme (specific activity: 90 mU/mg) was obtained by a purification process similar to that employed in section (1) of Reference Example 2 except that crude TP enzyme derived from *Kineosporia aurantiaca* ATCC 29727 in section (2) of Reference Example 1 was used instead of the crude TP enzyme derived from *Catellatospora ferruginea* KY2039.

The specific actifity of the purified TP enzyme was as 90 times as that of the crude enzyme, and the yield of the enzyme activity was 50%.

(3) To crude MP enzyme derived from *Propionibacterium freudenreichii* KY4002 in section (3) of Reference Example 1, ammonium sulfate was added to the concentration of 80% saturation to collect the precipitates. The obtained precipitates were dissolved in a small amount (about 20 ml) of 10 mM phosphate buffer (pH 7.0). The obtained solution was dialyzed against 2 L of the same buffer for 24 hours, heated at 50° C. for 15 minutes, and centrifuged (12,000×g, 20 minutes). The obtained supernatant was loaded onto the column (1 L, diameter: 5 cm) packed with anion exchange resin DEAE-Sephadex (Pharmacia LKB Biotechnology) which had previously been equilibrated with the same buffer to effect the adsorption. Contaminant proteins were washed off with the same buffer, and the gradient elution was conducted with 0 to 1.0M of sodium chloride (10 mM phosphate buffer, pH 7.0). The active fractions eluted at a sodium chloride concentration of about 0.5 to 0.8M were combined, and ammonium sulfate was added to the concentration of 80% saturation to obtain the precipitates. The obtained precipitates were collected by centrifugation (12,000×g, 20 minutes) and dissolved in 10 ml of 10 mM phosphate buffer (pH 7.0). The obtained solution was dialyzed against 2 L of the same buffer for 24 hours to obtain purified MP enzyme (specific activity: 50 mU/mg).

The specific activity of the purified MP enzyme was as 48 times as that of the crude enzyme, and the yield of the enzyme activity was 79%.

(4) Purified MP enzyme (specific activity: 45 mU/mg) was obtained by the purification process similar to that employed in section (3) of Reference Example 2 except that the crude MP enzyme derived from *Enterococcus faecium* ATCC 10541 in section (4) of Reference Example 1 was used instead of the crude MP enzyme derived from *Propionibacterium freudenreichii* KY4002. The specific activity of the purified MP enzyme was as 45 times as that of the crude enzyme, and the yield of the enzyme activity was 75%.

Industrial Applicability

According to the present invention, process for producing disaccharides efficiently at a low cost and the novel disaccharides obtained thereby are provided.

We claim:
1. A process for producing a disaccharide, which comprises:

condensing beta-glucose-1-phosphate in an aqueous medium with a) a monosaccharide selected from the group consisting of D-fucose and D-xylose in the presence of trehalose phosphorylase which is derived from a microorganism belonging to the genus Catellatospora and which acts on D-fucose and D-xylose, or b) a monosaccharide selected from the group consisting of D-mannose, D-allose D-tagatose, D-sorbose and L-Fucose in the presence of maltose phosphorylase which is derived from a microorganism belonging to the genus Propionibacterium and which acts on D-mannose, D-allose, D-tagatose, D-sorbose and L-fucose; and recovering the disaccharide formed in the aqueous medium.

2. The process according to claim 1, wherein said beta-glucose-1-phosphate is obtained by reacting trehalose in the presence of trehalose phosphorylase or by reacting maltose in the presence of maltose phosphorylase.

3. The process according to claim 1, wherein said beta-glucose-1-phosphate is obtained by a) reacting trehalose in the aqueous medium in the presence of trehalose phosphorylase which is derived from a microorganism belonging to the genus Catellatospora and which acts on D-fucose and D-xylose, or b) reacting maltose in the aqueous medium in the presence of maltose phosphorylase which is derived from a microorganism belonging to the genus Propionibacterium and which acts on D-mannose, D-allose, D-tagatose, D-sorbose and L-fucose.

4. The process according to claim 2 or 3, which comprises further adding an enzyme having glucose decomposition activity.

5. The process according to claim 4 wherein said enzyme having glucose decomposition activity is glucose oxidase, catalase, pyranose oxidase, glucose dehydrogenase, glucokinase or hexokinase.

6. Glucosyl ($\alpha$, 1-1) D-fucose.

7. Glucosyl ($\alpha$, 1-4)L-fucose.

8. The process according to claim 1, wherein the microorganism Catellatospora is *Catellatospora ferruginea*, and the Propionibacterium is *Propionibacterium freudenreichii*.

* * * * *